US008012490B2

(12) United States Patent
Palese et al.

(10) Patent No.: US 8,012,490 B2
(45) Date of Patent: Sep. 6, 2011

(54) RECOMBINANT INFLUENZA VIRUSES EXPRESSING TUMOR-ASSOCIATED ANTIGENS AS ANTITUMOR AGENTS

(75) Inventors: Peter Palese, Leonia, NJ (US); Adolfo Garcia-Sastre, New York, NY (US); Nicholas P. Restifo, Washington, DC (US)

(73) Assignees: Mount Sinai School of Medicine, New York, NY (US); The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 12/564,702

(22) Filed: Sep. 22, 2009

(65) Prior Publication Data

US 2010/0080827 A1 Apr. 1, 2010

Related U.S. Application Data

(60) Division of application No. 10/848,620, filed on May 17, 2004, now abandoned, which is a continuation of application No. 09/070,629, filed on Apr. 30, 1998, now Pat. No. 6,884,414.

(60) Provisional application No. 60/045,176, filed on Apr. 30, 1997.

(51) Int. Cl.
*A61K 39/00* (2006.01)
*A61K 39/145* (2006.01)

(52) U.S. Cl. ................ 424/199.1; 424/209.1; 424/277.1

(58) Field of Classification Search ........................ None
See application file for complete search history.

(56) References Cited

U.S. PATENT DOCUMENTS

| | | | |
|---|---|---|---|
| 4,690,915 A | 9/1987 | Rosenberg et al. |
| 5,081,029 A | 1/1992 | Zarling et al. |
| 5,166,057 A | 11/1992 | Palese et al. |
| 5,578,473 A | 11/1996 | Palese et al. |
| 5,854,037 A | 12/1998 | Palese et al. |
| 6,300,090 B1 | 10/2001 | Steinman et al. |

FOREIGN PATENT DOCUMENTS

WO WO 93/21306 10/1993

OTHER PUBLICATIONS

Akagi et al. "Therapeutic antitumor response after immunization with an admixture of recombinant vaccinia viruses expressing a modified MUC1 gene and the murine T-cell costimulatory molecule B7", J. Immunother. Jan. 1997; 20(1):38-47.

Ansardi et al., 1994, "Characterization of poliovirus replicons encoding carcinoembryonic antigen", Cancer Res. 54:6359-6364.

Bridgewater & Collins, "Vaccine Immunotherapy for Cancer," Chapter 8 in Dickson G, ed., Molecular and Cell Biology of Human Gene Therapeutics, 1995, Chapman & Hall, pp. 140-156.

Chen et al., 1996, "Therapeutic antitumor response after immunization with a recombinant adenovirus encoding a model tumor-associated antigen", J. Immunol. 156:224-231.

Conry et al., 1995, "A carcinoembryonic antigen polynucleotide vaccine has in vivo antitumor activity", Gene Ther. 2:59-65.

Declaration of Dr. Adolfo Garcia-Sastre Under 37 C.F.R. § 1.132, dated Jul. 14, 2003.

Durrant LG, Cancer vaccines. Anticancer Drugs. Sep. 1997;8(8):727.

Efferson et al., "Activation of Tumor Antigen-Specific Cytotoxic T Lymphocytes (CTLs) by Human Dendritic Cells Infected with an Attenuated Influenza A Virus Expressing a CTL Epitope Derived from the HER-2/neu Proto-Oncogene," 2003, J. Virol. 77:7411-7424.

Efferson et al., "Stimulation of Human T Cells by an Influenza A Vector Expressing a CTL Epitope from the HER-2/neu Protoooncogene Results in Higher Numbers of Antigen-specific TCRhi Cells than Stimulation with Peptide. Divergent Roles of IL-2 and IL-15," 2005, Anticancer Res. 25:715-724.

Enami and Palese, 1991, "High-efficiency formation of influenza virus transfectants", J. Virol. 65:2711-2713.

Garcia-Sastre et al., 1994, "Use of a mammalian internal ribosomal entry site element for expression of a foreign protein by a transfectant influenza virus", J. Virol. 68:6254-6261.

Garcia-Sastre and Palese, 1993, "Genetic manipulation of negative-strand RNA virus genomes", Annu. Res. Microbiol. 47:765-790.

Greenberg, 1991, "Adoptive T cell therapy of tumors: mechanisms operative in the recognition and elimination of tumor cells", Adv. Immunol. 49:281.

Hodge et al., 1995, "A recombinant vaccinia virus expressing human prostate-specific antigen (PSA): safety and immunogenicity in a non-human primate", Int. J. Cancer 63:231-237.

Houghton An, "On course for a cancer vaccine," 1995, The Lancet 345:1384-1385.

Irvine et al., 1996, "Cytokine enhancement of DNA immunization leads to effective treatment of established pulmonary metastases", J. Immunol. 156:238.

Irvine et al., 1995, "Synthetic oligonucleotide expressed by a recombinant vaccinia virus elicits therapeutic CTL", J. Immunol. 154:4651.

Itoh et al. "Development of cancer vaccine by tumor rejection antigens.", Int Rev Immunol. 1997;14(2-3):153 71. Review. Johanning et al., 1995, "A sindbis virus mRNA polynucleotide vector achieves prolonged and high level heterologous gene expression in vivo", Nucl. Acids Res. 23:1495-1501.

Kawakami et al. Human melanoma antigens recognized by T lymphocytes. Keio J Med. Jun. 1996;45(2):100-108.

Kawakami Y and Rosenberg SA., T-cell recognition of self peptides as tumor rejection antigens. Immunol Res. 1996;15(3):179-90. Review.

Krainer et al. Tissue expression and serum levels of HER-2/neu in patients with breast cancer. Oncology. Nov.-Dec. 1997;54(6):475-81.

Maeurer et al. New treatment options for patients with melanoma: review of melanoma derived T-cell epitope-based peptide vaccines. Melanoma Res. Feb. 1996;6(1):11-24. Review.

McCabe et al., 1995, "Minimal determinant expressed by a recombinant vaccinia virus elicits therapeutic antitumor cytolytic T lymphocyte responses", Cancer Res. 55:1741-7.

Moss, 1996, "Poxviridae: the viruses and their replication", in: Fields Virology, Fields et al., eds., Lippincott-Raven, Philadelphia, pp. 2637-2671.

(Continued)

*Primary Examiner* — Mary E Mosher

(74) *Attorney, Agent, or Firm* — Jones Day

(57) ABSTRACT

The present invention relates to the engineering of recombinant influenza viruses that express tumor-associated antigens. Expression of tumor-associated antigens by these viruses can be achieved by engineering specific epitopes into influenza virus proteins, or by engineering viral genes that encode a viral protein and the specific antigen as independent polypeptides. Tumor-bearing patients can be immunized with the recombinant influenza viruses alone, or in combination with another treatment, to induce an immune response that leads to tumor reduction. The recombinant viruses can also be used to vaccinate high risk tumor-free patients to prevent tumor formation in vivo.

13 Claims, 4 Drawing Sheets

OTHER PUBLICATIONS

Figure 1:
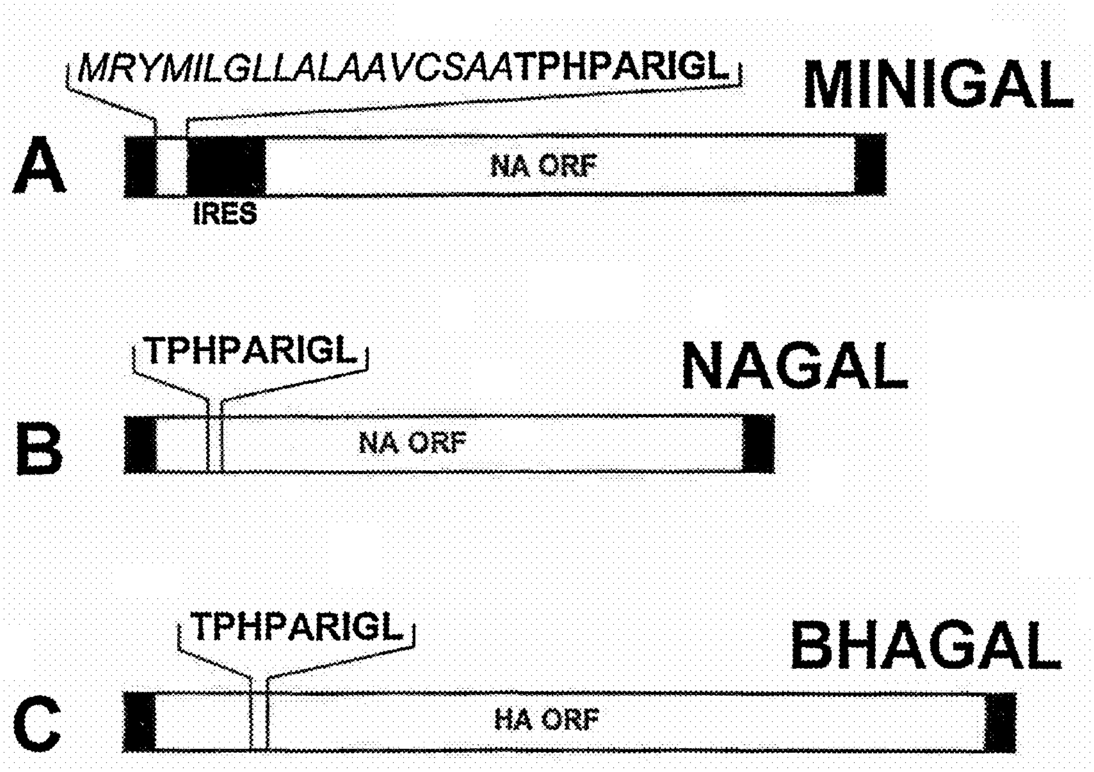

Murata et al., 1996, "Characterization of in vivo primary and secondary CD8+ T cell responses induced by recombinant influenza and vaccinia viruses", Cell. Immunol. 173:96.

Muster et al., 1995, "Mucosal model of immunization against human immunodeficiency virus type 1 with a chimeric influenza virus", J. Virol. 69:6678.

Muster et al., 1994, "Cross-neutralizing activity against divergent human immunodeficiency virus type 1 isolates induced by the gp41 sequence ELDKWAS", J. Virol. 68:4031-4034.

Osanto S. Vaccine Trials for the Clinician: Prospects for Tumor Antigens. Oncologist, 1997:2(5):284.

Pardoll DM., "Cancer Vaccines," 1998, Nature Medicine Vaccine Supplement 4(5):525-531.

Plotkin et al., 1995, "The safety and use of canarypox vectored vaccines", Dev. Biol. Stand. 84:165.

Randrianarison-Jewtoukoff and Perricaudet, 1995, "Recombinant adenoviruses as vaccines", Biologicals 23:145-157.

Rao et al., 1996, "IL-12 is an effective adjuvant to recombinant vaccinia virus-based tumor vaccines: enhancement by simultaneous B7-1 expression", J. Immunol. 156:3357-3365.

Restifo et al., "Transfectant Influenza A Viruses Are Effective Recombinant Immunogens in the Treatment of Experimental Cancer," 1998, Virology 249; 89-97.

Restifo NP, "Recombinant Anticancer Vaccines," 1996, The Cancer Journal from Scientific American 2(1):16-18.

Restifo, 1996, "The new vaccines: building viruses that elicit antitumor immunity", Curr. Opin. Immunol. 8:658.

Restifo et al., 1995, "Antigen processing in vivo and the elicitation of primary CTL responses", J. Immunol. 154:4414.

Robbins and Kawakami, 1996, "Human tumor antigens recognized by T cells", Curr. Opinion Immunol. 8: 628-636.

Rodrigues et al., 1994, "Influenza and vaccinia viruses expressing malaria CD8+ T and B cell epitopes. Comparison of their immunogenicity and capacity to induce protective immunity", J. Immunol. 153:4636.

Rosenberg et al., 1994, "Treatment of patients with metastatic melanoma with autologous tumor-infiltrating lymphocytes and interleukin 2", J. Natl. Cancer Inst. 86:1159-1166.

Rosenberg et al. "Immunizing patients with metastatic melanoma using recombinant adenoviruses encoding MART-1 or gp100 melanoma antigens", J Natl Cancer Inst. Dec. 16, 1998; 90(24):1894-900.

Strobel et al., 2000, "Efficient Expression of the Tumor-Associated Antigen MAGE-3 in Human Dendritic Cells, Using an Avian Influenza Virus Vector", Human Gene Therapy 11:2207-2218.

Wang et al., 1995, Active immunotherapy of cancer with a nonreplicating recombinant fowlpox virus encoding a model tumor.

Zhai et al. Cloning and characterization of the genes encoding the murine homologues of thc human melanoma antigens MART1 and gp100. J Immunother. Jan. 1997;20(1):15.

Zhai et al. Antigen-specific tumor vaccines. Development and characterization of recombinant adenoviruses encoding MART1 or gp100 for cancer therapy. J Immunol. Jan. 15, 1996;156(2):700-10.

RECOMBINANT INFLUENZA VIRUSES EXPRESSING TUMOR-ASSOCIATED ANTIGENS AS ANTITUMOR AGENTS

This application is a divisional of U.S. application Ser. No. 10/848,620, filed May 17, 2004, now abandoned, which is a continuation of U.S. application Ser. No. 09/070,629, filed Apr. 30, 1998, which issued as U.S. Pat. No. 6,884,414 on Apr. 26, 2005, which claims priority to U.S. provisional application Ser. No. 60/045,176, filed Apr. 30, 1997, each of which is incorporated by reference herein in its entirety.

The work reflected in this application was supported, in part, by a grant from the National Institutes of Health, and the Government may have certain rights in this invention.

1. INTRODUCTION

The present invention relates to the engineering of recombinant influenza viruses that express tumor-associated antigens. Expression of tumor-associated antigens by these viruses can be achieved by engineering specific epitopes into influenza virus proteins, or by engineering viral genes that encode a viral protein and the specific antigen as independent polypeptides. Tumor-bearing patients can be immunized with the recombinant influenza viruses alone, or in combination with another treatment, to induce an immune response that leads to tumor reduction. The recombinant viruses can also be used to vaccinate high risk tumor-free patients to prevent tumor formation in vivo.

2. BACKGROUND OF THE INVENTION

A number of immunotherapeutic approaches proposed for the treatment of tumors have had limited success. For example, the use of exogenous antibodies or immunotoxins specific for tumor associated antigens (TAAs) has been attempted for the targeted killing of tumor cells. However, successful treatment has been hampered, in part, by the relative inaccessibility of the tumor cells to the circulating, exogenously administered antibodies.

Other approaches have been designed to elicit a host immune response against the tumor cells. Indeed, there is strong evidence suggesting that the stimulation of a potent and specific T-cell response against tumor cells will result in tumor reduction. However, although most cancer cells express tumor associated antigens (TAAs), the presence of a tumor usually does not result in the induction of tumor-specific immunity. Attempts to increase the poor immunogenicity of tumor cells comprise most of the history of cancer immunotherapy. These efforts have included physical modification of the tumor cells (including γ-irradiation), the inoculation of mixtures of tumor cells and pathogens (viruses, bacteria and bacterial extracts) and more recently, gene-modification of the tumor cells with a variety of immunomodulatory molecules.

In the case of vaccination in the treatment and/or prevention of cancer, a potentially effective strategy for eliciting vigorous immune responses against TAAs may involve the insertion of the cloned genes encoding TAAs into recombinant viruses (reviewed in Restifo, 1996, Curr. Opin. Immunol. 8:658-663). A number of recombinant expression vectors have been shown to be useful in the prevention, and in some cases in the treatment, of tumors in experimental animals including poxviruses (vaccinia (Hodge, et al., 1995, Int. J. Cancer 63:231-237)), fowlpox (Wang, et al., 1995, J. Immunol. 154:4685-4692) and canary pox (Plotkin, et al., 1995, Dev. Biol. Stand. 84:165-170)); adenoviruses (Chen, et al., 1996, J. Immunol. 156:224-231; Randrianarison-Jewtoukoff and Perricaudet, 1995, Biologicals 23:145-157); polioviruses (Ansardi, et al., 1994, Cancer Res. 54:6359-6364); Sindbis viruses (Johanning, et al., 1995, Nucleic Acids Res. 23:1495-1501) and non-viral vectors including plasmid DNA administered by injection (Conry, et al., 1995, Gene Ther. 2:59-65) and by "gene gun" (Irvine, et al., 1996, J. Immunol. 156:238-245).

However, the foregoing systems have limitations which restrict their use in humans. For example, pre-existing immunity to vaccinia or adenovirus precludes their use as vaccinating strains. Moreover, the immune response induced by vaccinia or adenovirus precludes the use of the same virus for a second immunization or boost. In addition, the pathogenicity associated with some virus vectors, e.g., adenoviruses, also severely limit their use in vaccine formulations for human patients. Thus, there is a need for the continued exploration of new vector systems for use in cancer vaccines.

3. SUMMARY OF THE INVENTION

The invention relates to recombinant influenza viruses that express TAAs, and their use to "immunize" tumor-bearing hosts in order to generate an immune response that leads to tumor regression. Alternatively, tumor-free subjects who have a predisposition to develop tumors can be immunized or vaccinated with the recombinant influenza viruses of the invention to prevent tumor formation.

Expression of TAAs by these viruses can be achieved by engineering specific TAA epitopes into the influenza virus proteins, or by engineering viral genes that encode a viral protein and the specific antigen as independent polypeptides. The methods of the present invention permit the generation of stable recombinant viruses expressing foreign epitopes and/or polypeptides.

Reverse genetics techniques to engineer influenza viruses are described. Immunization of tumor-bearing patients with such viruses alone, or in combination with another treatment, to induce an immune response that leads to tumor reduction is also described. For example, the recombinant influenza viruses of the invention can be used to immunize or "vaccinate" a tumor-bearing host in order to generate an immune response against tumor cells. The antitumor immune response can be enhanced by a subsequent "booster" immunization using a subunit vaccine preparation containing the appropriate TAA, a different viral vector (e.g., a pox virus based vector) that expresses the TAA, or TAA expressed by an influenza recombinant engineered using a serotype that differs from the initial inoculant. The immunization protocol may be used alone or in conjunction with surgical, radiation or chemotherapeutic regimens. Alternatively, tumor-free hosts can be similarly vaccinated to prevent tumor formation in vivo.

The invention is based, in part, on the surprising discovery that the recombinant influenza viruses of the invention induce a potent and specific cell-mediated immune response directed against the tumor cells resulting in tumor reduction. The invention is also based, in part, on the recognition that non-transmissible attenuated strains of influenza virus could be used to engineer vaccines for use in humans. Moreover, since influenza viruses change their antigenic determinants very quickly, different viral strains can be selected and engineered for use to avoid the presence of pre-existing immunity against the virus in patients. Strain variability permits the construction of a vast repertoire of vaccine formulations, and obviates the problems of host resistance.

The invention is illustrated by way of working examples which demonstrate the invention in a murine model. Strikingly, mice immunized with a recombinant influenza A virus vector, and boosted with a vaccinia virus vector expressing the same antigen were able to generate high levels of CTLs against the expressed antigen. Treatment with the recombinant influenza virus vectors mediated regression of an experimental established murine cancer.

3.1. Abbreviations

CTL, cytotoxic lymphocyte
β-gal, β-galactosidase
HA, hemagglutinin
IRES, internal ribosomal entry site
MOI, multiplicity of infection
NA, neuraminidase
PFU, plaque forming units
TAA, tumor-associated antigen

4. DESCRIPTION OF THE FIGURES

FIG. 1. Schematic representation of the recombinant genes of the transfectant influenza viruses expressing the CD8+T-cell β-gal epitope TPHPARIGL (SEQ ID NO:1).

A. MINIGAL recombinant gene. The β-gal epitope is expressed downstream of a leader peptide (characters in italics) (SEQ ID NO:2) as an independent polypeptide from a bicistronic NA gene. Expression of the viral NA protein in this gene is achieved via internal initiation of translation mediated by an IRES element derived from the BiP mRNA (Garcia-Sastre, et al., 1994, J. Virol. 68:6254-6261).

B. NAGAL. The β-gal epitope is expressed as part of the amino acid sequence of the NA protein.

C. BHAGAL. The β-gal epitope is expressed as part of the amino acid sequence of the HA protein. The NA and HA open reading frames (ORF) are indicated. Black boxes represent noncoding regions in the represented genes.

Figure 2:
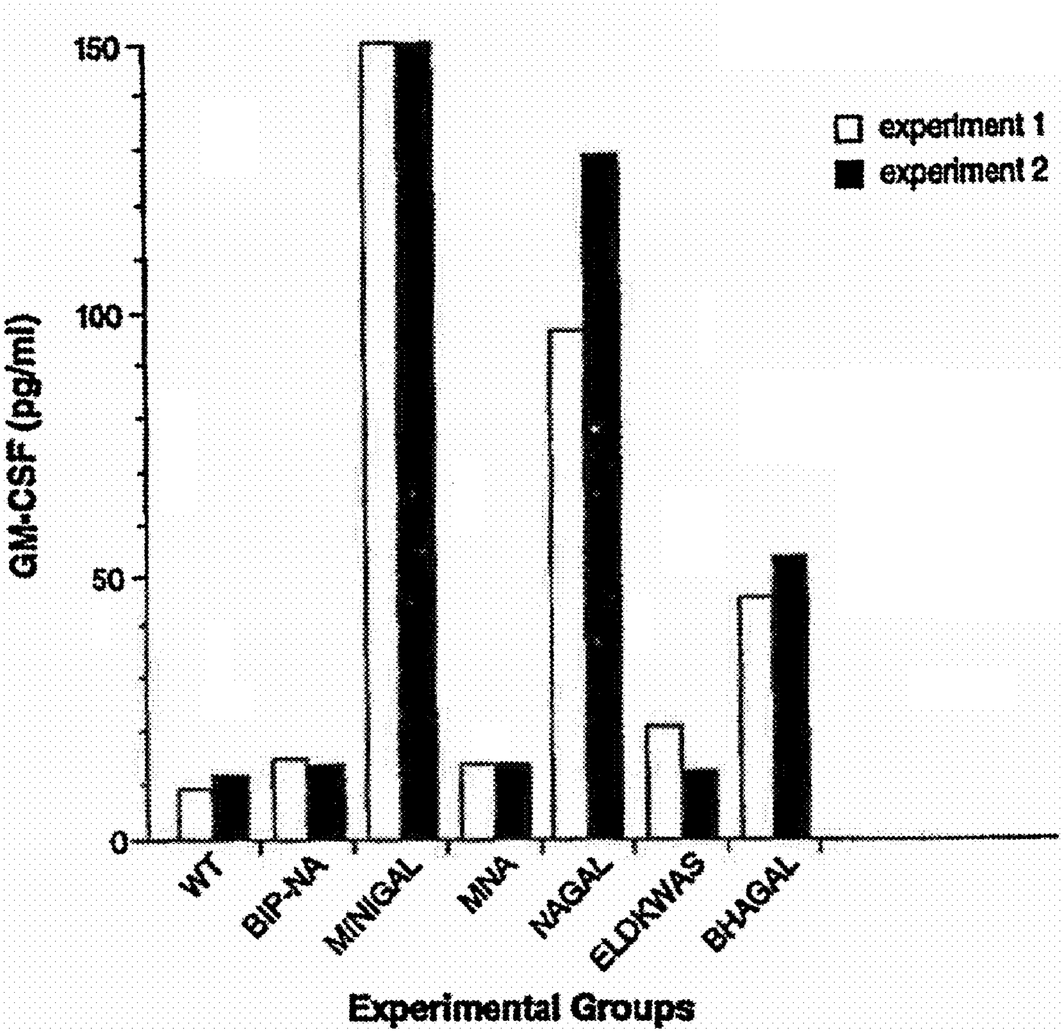

FIG. 2. Specific recognition of transfectant influenza A virus-infected cells by a β-gal-specific CTL clone. Five$\times10^5$ CT26.WT cells/well (24 well plate) were incubated in RPMI, 0.1% BSA, 30 mM HEPES at pH 6.8, and they were infected with the influenza viruses shown at an MOI of 5 for 3 hours. Specific CTLs against the β-gal epitope TPHPARIGL (SEQ ID NO:1) were then added at an E:T ratio of 1. After 24 hours of coincubation cell supernatants were harvested and assayed for GM-CSF. Results from two independent experiments are represented. WT, influenza A/WSN/33 wild-type virus.

Figure 3:
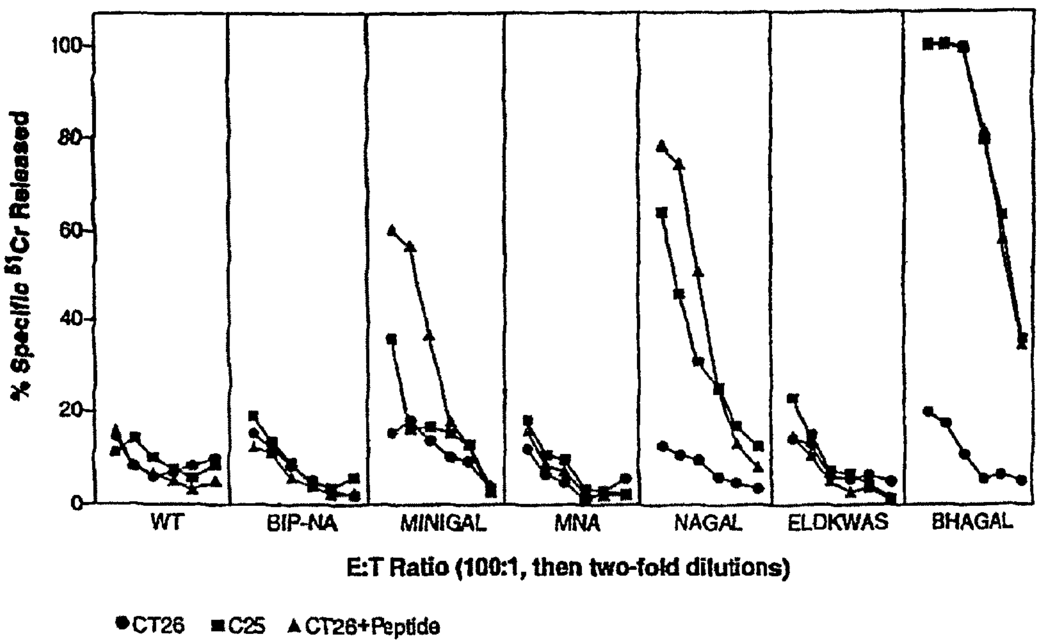

FIG. 3. Specific cytolytic responses induced in mice by transfectant influenza A viruses expressing the β-gal epitope TPHPARIGL (SEQ ID NO:1). To evaluate the function of transfectant influenza A viruses in the priming of β-gal-specific cytotoxic responses in vivo, two mice/group were infected with the influenza A virus shown on the abscissa. Three weeks latter, splenocytes from immunized mice were cultured in the presence of the $L^d$-restricted β-gal876-884 peptide for 6 days then tested in a microcytotoxicity assay against CT26.WT, CT26.CL25 or CT26.WT cells loaded with the β-gal876-884 peptide, at the indicated E:T ratios. Experiment was performed two additional times with similar results.

Figure 4:
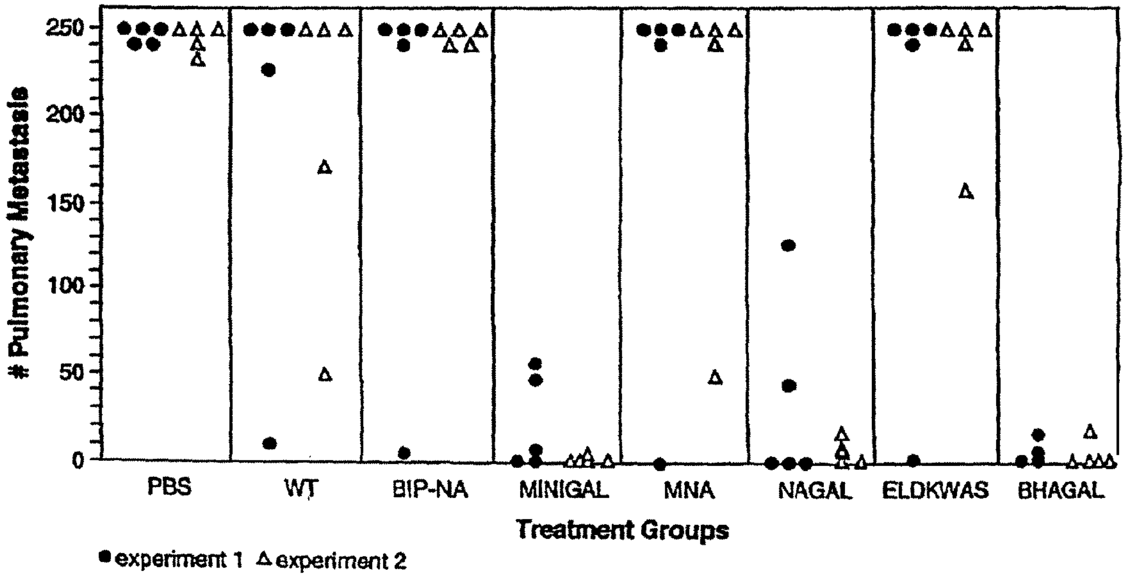

FIG. 4. Transfectant influenza A viruses mediate treatment of pulmonary metastases established for three days. Mice were inoculated intravenously with $5\times10^6$ CT26.CL25 tumor cells, then vaccinated three-days later with $10^6$ pfu of the transfectant influenza A virus shown. Twelve hours after the therapeutic immunization, mice were given 100,000 Cetus units of rIL-2 bid for 3 days. The lungs of treated mice were evaluated in a coded, blinded manner for pulmonary metastases 12 days after the tumor inoculation. The number of pulmonary metastases that were enumerated after two independent experiments are shown for individual mice.

5. DETAILED DESCRIPTION OF THE INVENTION

The engineering of recombinant influenza viruses expressing TAAs, and their use as immunogenic compositions or vaccines to induce tumor regression in mammals, including humans, is described. One drawback to the use of viruses such as vaccinia for constructing recombinant or chimeric viruses for use in vaccines is the lack of variation in its major epitopes. This lack of variability in the viral strains places strict limitations on the repeated use of chimeric vaccinia virus, in that a first vaccination will generate host resistance to the strain so that the same virus cannot infect the host in a second inoculation. Inoculation of a resistant individual with chimeric vaccinia virus will, therefore, not induce immune stimulation. The considerable advantage of using influenza virus, a negative-strand RNA virus, for vaccination, is that it demonstrates a wide variability of its major epitopes. Thousands of variants of influenza virus have been identified, each strain evolving by antigenic drift.

"Reverse genetics" techniques are used to construct recombinant and/or chimeric influenza virus templates engineered to direct the expression of heterologous gene products. When combined with purified viral RNA-directed RNA polymerase, these virus templates are infectious, replicate in hosts, and their heterologous gene is expressed and packaged by the resulting recombinant influenza viruses (For a description of the reverse genetics approach see Palese et al., U.S. Pat. No. 5,166,057 and Palese, WO93/21306, each of which is incorporated by reference herein in its entirety). The expression products and/or chimeric virions obtained can be used in vaccine formulations, and the strain variability of the influenza virus permits construction of a vast repertoire of vaccine formulations and obviates the problem of host resistance. Furthermore, influenza virus stimulates a vigorous cytotoxic T cell response. Hence, the presentation of foreign epitopes in an influenza virus background can further induce secretory immunity and cell-mediated immunity.

5.1. Construction of the Recombinant Influenza A Virus

In accordance with the invention, recombinant influenza viruses are engineered to express tumor-associated antigens (TAAs), including, but not limited to, the TAAs set forth in Table 1.

TABLE 1

| Human tumor antigens recognized by T cells (Robbins and Kawakami, 1996, Curr. Opin. Immunol. 8: 628-636) |
|---|
| Melanocyte lineage proteins |
| gp100 |
| MART-1/MelanA |
| TRP-1 (gp75) |
| Tyrosinase |
| Tumor-specific, widely shared antigens |
| MAGE-1 |
| MAGE-3 |
| BAGE |
| GAGE-1, -2 |

TABLE 1-continued

| Human tumor antigens recognized by T cells (Robbins and Kawakami, 1996, Curr. Opin. Immunol. 8: 628-636) |
|---|
| N-acetylglucosaminyltransferase-V |
| p15 |
| Tumor-specific, mutated antigens |
| β-catenin |
| MUM-1 |
| CDK4 |
| Nonmelanoma antigens |
| HER-2/neu (breast and ovarian carcinoma) |
| Human papillomavirus-E6, E7 (cervical carcinoma) |
| MUC-1 (breast, ovarian and pancreatic carcinoma) |

Indeed, antigens which are identified in the future as TAAs are included within the scope of the invention for the construction of recombinant influenza viruses by the techniques described herein. The selection of the TAA or its epitope will depend upon the tumor type to be treated.

The use of reverse genetics to genetically engineer influenza viruses, including attenuated influenza viruses, and methods for their production, are described in Palese et al. (U.S. Pat. No. 5,166,057) and Palese (WO93/21306). Such reverse genetics techniques can be utilized to engineer a mutation, including but not limited to an insertion, deletion, or substitution of an amino acid residue(s), an antigen(s), or an epitope(s) into a coding region of the viral genome so that altered or chimeric viral proteins are expressed by the engineered virus. Alternatively, the virus can be engineered to express the TAA as an independent polypeptide.

The reverse genetics technique involves the preparation of synthetic recombinant viral RNAs that contain the non-coding regions of the negative strand virus which are essential for the recognition of viral RNA by viral polymerases and for the packaging into mature virions. The recombinant RNAs are synthesized from a recombinant DNA template and reconstituted in vitro with purified viral polymerase and nucleoprotein complex to form recombinant ribonucleoproteins (RNPs) which can be used to transfect cells.

Preferably, the viral polymerase proteins are present during in vitro transcription of the synthetic RNAs prior to transfection. The synthetic recombinant RNPs can be rescued into infectious virus particles. The foregoing techniques are described in Palese et al., U.S. Pat. No. 5,166,057, and in Enami and Palese, 1991, J. Virol. 65:2711-2713, each of which is incorporated by reference herein in its entirety.

Such reverse genetics techniques can be used to insert a TAA or an epitope of TAA into an influenza virus protein so that a chimeric protein is expressed by the virus. While any of the influenza viral proteins may be engineered in this way, the influenza HA or NA proteins are preferred when it is desired to engineer the expression of the TAA or epitope on the surface of the recombinant influenza virus.

Alternatively, viral genes can be engineered to encode a viral protein and the specific TAA as independent polypeptides. To this end, reverse genetics can advantageously be used to engineer a bicistronic RNA segment as described in U.S. Pat. No. 5,166,057 and in co-pending application Ser. No. 08/252,508 filed Jun. 1, 1994 (allowed), each of which is incorporated by reference in its entirety herein; i.e., so that the engineered viral RNA species directs the production of both the viral protein and the TAA as independent polypeptides.

Attenuated strains of influenza may be used as the "parental" strain to generate the influenza recombinants. Alternatively, reverse genetics can be used to engineer both the attenuation characteristics as well as the TAA or TAA epitope into the recombinant influenza viruses of the invention.

In one embodiment, reverse genetics methods can be used to construct an influenza A virus transfectant that encodes a fragment or portion of a TAA, e.g., MART-1 or gp100 (melanoma TAAs). More preferably, sequences encoding such epitopes or fragments thereof are nested within an open reading frame, e.g., the hemagglutinin (HA) or neuraminidase (NA) open reading frames.

In another embodiment, an independent minigene encoding a fragment or portion of an epitope, e.g., a minigene encoding a TAA or fragment thereof, is preceded by an endoplasmic reticulum insertion signal sequence, placed in a bicistronic arrangement in the NA RNA segment of the recombinant influenza A virus. Preferably, a transfectant expressing such a minigene mediates the presentation of the epitope to an anti-epitope CTL clone, and elicits specific cytolytic responses in vivo. Most preferably, such a transfectant, when administered in a vaccine formulation, mediates the regression of a tumor, metastasis, or neoplastic growth.

5.2. Vaccine Formulations Using The Recombinant Viruses

The recombinant influenza viruses can be formulated as immunogenic compositions, which may be referred to herein as vaccines.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations maybe accomplished using conventional methods involving propagation of the virus in cell culture or in the allantois of the chick embryo followed by purification.

In this regard, the use of genetically engineered influenza virus (vectors) for vaccine purposes may require the presence of attenuation characteristics in these strains. Current live virus vaccine candidates for use in humans are either cold adapted, temperature sensitive, or passaged so that they derive several (six) genes from avian viruses, which results in attenuation. The introduction of appropriate mutations (e.g., deletions) into the templates used for transfection may provide the novel viruses with attenuation characteristics. For example, specific multiple missense mutations which are associated with temperature sensitivity or cold adaption can be made into deletion mutations and/or multiple mutations can be introduced into individual influenza virus genes. These mutants should be more stable than the cold or temperature sensitive mutants containing single point mutations and reversion frequencies should be extremely low.

Alternatively, recombinant viruses with "suicide" characteristics may be constructed. Such viruses would go through only one or a few rounds of replication in the host. For example, cleavage of the hemagglutinin envelope glycoprotein (HA) is necessary to allow for reinitiation of replication. Therefore, changes in the HA cleavage site may produce a virus that replicates in an appropriate cell system but not in the human host. When used as a vaccine, the recombinant virus would go through a single replication cycle and induce a sufficient level of immune response but it would not go further in the human host and cause disease. Recombinant viruses lacking one or more of the essential influenza virus genes would not be able to undergo successive rounds of replication. Such defective viruses can be produced by co-transfecting reconstituted RNPs lacking a specific gene(s) into cell lines which permanently express this gene(s).

Viruses lacking an essential gene(s) will be replicated in these cell lines but when administered to the human host will not be able to complete a round of replication. Such preparations may transcribe and translate—in this abortive cycle—a sufficient number of genes to induce an immune response. Alternatively, larger quantities of the strains could be administered, so that these preparations serve as inactivated (killed) virus, vaccines. For inactivated vaccines, it is preferred that the heterologous gene product be expressed as a viral component, so that the gene product is associated with the virion. The advantage of such preparations is that they contain native proteins and do not undergo inactivation by treatment with formalin or other agents used in the manufacturing of killed virus vaccines.

In another embodiment of this aspect of the invention, inactivated vaccine formulations may be prepared using conventional techniques to "kill" the recombinant viruses. Inactivated vaccines are "dead" in the sense that their infectivity has been destroyed. Ideally, the infectivity of the virus is destroyed without affecting is immunogenicity. In order to prepare inactivated vaccines, the recombinant virus may be grown in cell culture or in the allantois of the chick embryo, purified by zonal ultracentrifugation, inactivated by formaldehyde or β-propiolactone, and pooled. The resulting vaccine is usually inoculated intramuscularly.

Inactivated viruses may be formulated with a suitable adjuvant in order to enhance the immunological response. Such adjuvants may include but are not limited to mineral gels, e.g., aluminum hydroxide; surface active substances such as lysolecithin, pluronic polyols, polyanions; peptides; oil emulsions; and potentially useful human adjuvants such as BCG and *Corynebacterium parvum*.

5.3. Methods of Treatment and/or Vaccination

The recombinant influenza viruses of the invention can be used to treat tumor-bearing mammals, including humans, to generate an immune response against the tumor cells leading to tumor regression in vivo. The "vaccines" of the invention can be used either alone or in combination with other therapeutic regimens, including but not limited to chemotherapy, radiation therapy, surgery, bone marrow transplantation, etc. for the treatment of tumors. For example, surgical or radiation techniques could be used to debulk the tumor mass, after which, the vaccine formulations of the invention can be administered to ensure the regression and prevent the progression of remaining tumor masses or micrometastases in the body. Alternatively, administration of the "vaccine" can precede such surgical, radiation or chemotherapeutic treatment.

Alternatively, the recombinant viruses of the invention can be used to immunize or "vaccinate" tumor-free subjects to prevent tumor formation. With the advent of genetic testing, it is now possible to predict a subject's predisposition for cancers. Such subjects, therefore, may be immunized using a recombinant influenza virus expressing an appropriate tumor-associated antigen.

Many methods may be used to introduce the vaccine formulations described above into a patient. These include, but are not limited to, oral, intradermal, intramuscular, intraperitoneal, intravenous, subcutaneous, intranasal, transdermal, epidural, pulmonary, gastric, intestinal, rectal, vaginal, or urethral routes. When the method of treatment uses a live recombinant influenza vaccine formulation of the invention, it may be preferable to introduce the formulation via the natural route of infection of the influenza virus, i.e., through a mucosal membrane or surface, such as an oral, nasal, gastric, intestinal, rectal, vaginal or urethral route. To induce a CTL response, the mucosal route of administration may be through an oral or nasal membrane. Alternatively, an intramuscular or intraperitoneal route of administration may be used. Preferably, a dose of $10^6$-$10^7$ PFU (plaque forming units) of cold adapted recombinant influenza virus is given to a human patient.

The ability of influenza virus to induce a vigorous secretory and cellular immune response may be used advantageously. For example, infection of the respiratory tract by recombinant influenza viruses may induce a strong secretory immune response in a particular tissue or organ system, for example, the urogenital system.

Where subsequent or booster doses are required, a different serotype of influenza can be selected as the parental virus used to generate the recombinant. Alternatively, another virus such as vaccinia, or a subunit preparation can be used to boost. Immunization and/or cancer immunotherapy may be accomplished using a combined immunization regimen, e.g., immunization with a recombinant influenza viral vaccine of the invention and a boost of a recombinant vaccinia viral vaccine. In such an embodiment, a strong secondary $CD8^+$ T cell response is induced after priming and boosting with different viruses expressing the same epitope (for such methods of immunization and boosting, see, e.g., Murata et al., Cellular Immunol. 173:96-107). For example, a patient is first primed with a vaccine formulation of the invention comprising a recombinant influenza virus expressing an epitope, e.g., a selected TAA or fragment thereof. The patient is then boosted, e.g., 21 days later, with a vaccine formulation comprising a recombinant vaccinia virus expressing the same epitope. Such priming followed by boosting induces a strong secondary $CD8^+$ T cell response. Such a priming and boosting immunization regimen is preferably used to treat a patient with a tumor, metastasis or neoplastic growth expressing the selected TAA.

In yet another embodiment, the recombinant influenza viruses can be used as a booster immunization subsequent to a primary immunization with inactivated tumor cells, a subunit vaccine containing the TAA or its epitope, or another recombinant viral vaccine, such as vaccinia or adenovirus.

In an alternate embodiment, recombinant influenza virus encoding a particular TAA, epitope or fragment thereof may be used in adoptive immunotherapeutic methods for the activation of T lymphocytes that are histocompatible with the patient and specific for the TAA (for methods of adoptive immunotherapy, see, e.g., Rosenberg, U.S. Pat. No. 4,690,915, issued Sep. 1, 1987; Zarling, et al., U.S. Pat. No. 5,081,029, issued Jan. 14, 1992). Such T lymphocytes may be isolated from the patient or a histocompatible donor. The T lymphocytes are activated in vitro by exposure to the recombinant influenza virus of the invention. Activated T lymphocytes are expanded and inoculated into the patient in order to transfer T cell immunity directed against the TAA epitope.

6. EXAMPLE

Transfectant Influenza A Viruses as Effective and Safe Recombinant Immunogens in the Treatment of Cancer In the following example, reverse genetic methods were used to construct three different influenza A virus transfectants that encoded an $L^d$-restricted, nine amino acid long fragment of β-galactosidase (corresponding to residues 876-884). Sequences encoding this epitope were nested within the hemagglutinin (HA) or neuraminidase (NA) open reading frames. Alternatively, an independent β-galactosidase (β-gal) minigene, preceded by an endoplasmic reticulum insertion signal sequence, was placed in a bicistronic arrangement in the NA RNA segment of the virus. All three transfectants mediated the presentation of the epitope to an anti-β-gal CTL clone. Furthermore, each of the three transfectant viruses expressing the β-gal fragment elicited specific cytolytic responses in vivo. Most importantly, these transfectants mediated the regression of established murine pulmonary metastases.

The following example also demonstrates the efficacy of transfectant influenza viruses expressing a TAA to clear tumors in a murine cancer model. The experimental murine tumor used, CT26, was transfected with the lacZ gene, which encodes the enzyme β-galactosidase (β-gal). Hence β-gal was used in this system as the model TAA. Transfectant influenza viruses were engineered that expressed a CTL epitope from the model β-gal antigen. Then, the ability of these viruses to induce a therapeutic cellular immune response in mice bearing tumors expressing β-gal was determined. The results demonstrate that influenza virus vectors may be used in cancer immunotherapy.

6.1. Materials and Methods 6.1.1. Animals and Cell Lines

Six- to eight-week old female BALB/C (H-$2^d$) mice were obtained from Frederick Cancer Research Center (Frederick, Md.). CT26 is an N-nitroso-N-methylurethane induced BALB/C (H-$2^d$) undifferentiated colon carcinoma. The cloning of this tumor cell line to produce CT26.WT and the subsequent transduction with lacZ and subcloning to generate CT-26.CL25 which stably expresses β-gal, has been described previously (Wang, et al., 1995, J. Immunol. 154: 4685-4692).

These cell lines were maintained in RPMI 1640, 10% heat inactivated FCS (Biofluids, Rockville, Md.), 0.03% L-glutamine, 100 μg/m, streptomycin, 100 μg/ml penicillin and 50 μg/ml gentamicin sulfate (NIH Media Center). In addition, 400 or 800 μg/ml G418 (GIBCO, Grand Island, N.Y.) was added to the maintenance media of the CT26.CL25 cells. Madin-Darby bovine kidney (MDBK) cells were used for growing wild-type influenza A/WSN/33 virus and for rescuing and growing transfectant influenza viruses. MDBK cells were maintained in reinforced minimal essential medium containing 10% heat inactivated FCS (GIBCO, Grand Island, N.Y.)

6.1.2. Construction and Characterization of Transfectant Influenza A Viruses (FIG. 1)

The construction of the transfectant influenza viruses BIP-NA, MNA and ELDKWAS which were used in control experiments has been described (Garcia-Sastre, et al., 1994, J. Virol. 68:6254-6261; Rodrigues, et al., 1994, J. Immunol. 153:4636-4648; Muster, et al., 1994, J. Virol. 68:4031-4034). Transfectant viruses which express the $L^d$-restricted β-gal epitope TPHPARIGL (SEQ ID NO:1) were obtained by RNP-transfection as previously described (Garcia-Sastre and Palese, 1993, Annu. Rev. Microbiol. 47:765-790). These viruses contain one RNA segment which is derived from genetically engineered plasmid cDNA encoding the neuraminidase (NA) or hemagglutinin (HA) genes of influenza A/WSN/33 virus. One virus, called MINIGAL, encodes the amino acid sequence MRYMILGLLALAAVCSAATPHPARIGL (SEQ ID NO:2) from a minicistron followed by a mammalian internal ribosomal entry site (IRES) element just upstream of the NA open reading frame. Amino acid residues in front of the β-gal epitope TPHPARIGL (SEQ ID NO:1) are derived from the leader peptide of the E3/19K protein (Restifo, et al., 1995, J. Immunol. 154:4414-4422). A control virus, BIPNA, contains the same IRES sequences upstream of the NA open reading frame but lacks the β gal minicistron (Garcia-Sastre, et al., 1994, J. Virol. 68:6254-6261). The second transfectant virus, NAGAL, encodes for the amino acid sequence TPHPARIGL (SEQ ID NO:1) inserted in the stalk region of the NA protein. The third transfectant influenza virus, BHAGAL, encodes the same β-gal epitope inserted into the antigenic site B of the viral HA protein. MNA and ELDKWAS viruses, which contain irrelevant epitope insertions in the same context as NAGAL and BHAGAL viruses, respectively, were used as controls. Transfectant viruses were plaque purified three times in MDBK cells and their identities were subsequently confirmed by RT-PCR and sequencing of gene regions containing the engineered foreign sequences (Garcia-Sastre, et al., 1994, J. Virol. 68:6254-6261).

6.1.3. Peptides

The synthetic peptide TPHPARIGL (SEQ ID NO:1) was synthesized by Peptide Technologies (Washington D.C.) to a purity of greater than 99% as assessed by HPLC and amino acid analysis. This peptide represents the naturally processed H-2 $L^d$ restricted epitope spanning amino acids 876-884 of β-gal.

6.1.4. $^{51}$Chromium Release Assays

Six-hour $^{51}$Cr release assays were performed as previously described. Briefly, $2\times10^6$ target cells were incubated with 200 mCi $Na^{51}CrO_4$($^{51}$Cr) for ninety minutes. Peptide pulsed CT26.WT cells were incubated with 1 μg/ml of synthetic peptide during labeling. Target cells were then mixed with effector cells for six hours at the effector to target (E:T) ratios indicated. The amount of $^{51}$Cr released was determined by γ-counting and the percentage of specific lysis was calculated from triplicate samples as follows: [(experimental cpm−spontaneous cpm/maximal cpm−spontaneous cpm)]×100.

6.1.5. IN VITRO Stimulation of β-gal-specific Cytotoxic T Cells $10^5$ CT26.WT cells/well in 96 well, U-bottom plates (Costar,) were incubated in complete medium (RPMI, 0.1% BSA, 30 mM HEPES at Ph 6.8) and infected with the influenza viruses shown at a multiplicity of infection (MOI) of 20 for 3 hours. $CTL_x$, which are specific for the β-gal epitope were then added at an E:T of 1. After 24 hours of coincubation, supernatants were harvested and assayed for GM-CSF.

6.1.6. IN VIVO Experiments

Active treatment studies involved BALB/c mice inoculated intravenously with $5\times10^5$ CT2.CL25 cells. Three days later, mice were randomized, then inoculated with $10^6$ PFU of the indicated transfectant or wild-type influenza virus. Twelve days after tumor injection, mice were ear tagged, randomized again, and sacrificed. Lung metastases were enumerated in a blinded fashion by an investigator with no knowledge of the experimental groups.

6.1.7. Statistical Analysis

Data concerning the number of lung metastases do not follow a nominal distribution (since all lungs that contain >250 metastases were deemed too numerous to count) and thus were analyzed using the non-parametric two tailed Kruskal-Wallis test. All statistical values expressed are $P_2$ values.

6.2. Results 6.2.1. Rescue of Transfectant Influenza A Viruses Encoding a T Cell Epitope from β-galactosidase Recombinant viruses encoding a single $CD8^+$ T cell antigenic determinant of 8-10 amino acids in length can mediate the regression of experimental tumors (Irvine, et al., 1995, J. Immunol. 154:4651-4657; McCabe, et al., 1995, Cancer Res. 55:1741-1747; Restifo, 1996, Curr. Opin. Immunol. 8:658-663). Thus transfectant influenza A viruses were constructed that expressed the epitope TPHPARIGL (SEQ ID NO:1).

This determinant corresponds to amino acids 876-884 in the intact β-gal protein and is presented by the MHC class I Ld-molecule on the surface of the CT26.CL25 mouse tumor cells (Wang, et al., 1995, J. Immunol. 154:4685-4692).

Three different influenza A virus transfectants were generated (FIG. 1). The first transfectant virus, called MINIGAL, contained a minigene in a bicistronic arrangement within the NA-specific viral RNA segment. mRNA derived from this segment uses a mammalian IRES placed downstream of the minigene and upstream of the NA gene to achieve translation of the NA protein. In addition, the minigene is translated following the usual cap-dependent initiation of translation in eukaryotic cells. In this transfectant virus, the minigene was engineered to encode the E3/19K leader sequence at the N-terminus of the β-gal epitope TPHPARIGL (SEQ ID NO:1). The ER-insertion signal sequence has been found, in some cases, to greatly augment the immunogenicity of the encoded epitope (Restifo, et al., 1995, J. Immunol. 154:4414-4422). The control virus for this construct, designated BIPNA virus, employs the same IRES upstream of NA open reading frame but does not contain the β-gal epitope minigene (Garcia-Sastre, et al., 1994, J. Virol. 68:6254-6261). The second virus, NAGAL, encodes for the amino acid sequence TPHPARIGL (SEQ ID NO:1) inserted in the stalk region of the NA protein. The control for this construct is the MNA transfectant virus, which contains the irrelevant peptide SYVPSAEQI (SEQ ID NO:4) inserted into the NA stalk. This sequence is derived from the CS protein of *P. yoelii* (Rodrigues, et al., 1994, J. Immunol. 153:4636-4648). The third virus called BHAGAL encodes the β-gal epitope inserted into the antigenic site B of the HA protein. The control for this virus is designated ELDKWAS virus, which contains the gp41 HIV-derived sequence ELDKWAS (SEQ ID NO:3) inserted into the same domain of the HA (Muster, et al, 1995, J. Virol. 69:6678-6686).

Transfectant viruses MINIGAL, NAGAL and BHAGAL were rescued following RNP transfections into helper influenza virus infected cells. Sequence analysis of the rescued viruses confirmed the presence of the foreign β-gal-derived sequences. Viral titers obtained in MDBK cells for the transfectant viruses expressing the β-gal-epitope were comparable to the control transfectant viruses BIPNA, MNA and ELDKWAS and slightly lower (approximately one log) than wild-type influenza A/WSN/33 virus.

6.2.2. Transfectant Influenza Virus-Infected Cells are Able to Specifically Present the β-gal-epitope to $CD8^+$ T Cells To ascertain if the β-gal-epitope expressed by the transfectant influenza viruses could be processed and presented in the context of MHC class I molecules, CT26.WT tumor cells were infected with the different transfectant influenza A viruses encoding the β-gal epitope TPHPARIGL (SEQ ID NO:1), or the control viruses. Infected cells were then co-incubated for 24 hours with a $CD8^+$ T lymphocyte clone specific for this epitope. Supernatants were then assayed for GM-CSF, and the results are shown in FIG. 2. Cells that were infected with MINIGAL, NAGAL and BHAGAL viruses elicited specific release of GM-CSF. Neither control transfectant virus- or wild-type virus-infected cells were recognized by the β-gal-specific CTLs. Thus, the transfectant influenza A viruses were found to mediate the expression of the $L^d$-restricted β-gal epitope in forms that could be processed and presented at the surface of infected cells.

6.2.3. Transfectant Influenza A Viruses Elicit a β-gal Specific Cytolytic Response in Mice Cytolytic responses mediated by $CD8^+$ T lymphocytes specific for TAA play an important role in the regression of established tumor in both mouse and man (Greenberg, 1991, Adv. Immunol. 49:281-355; Rao, et al., 1996, J. Immunol. 156:3357-3365; Rosenberg, 1994, J. Natl. Cancer. Inst. 86:1159-1166). To evaluate the function of transfectant influenza A viruses in the priming of β-gal-specific cytotoxic responses in vivo, we immunized mice with the panel of influenza A viruses. Three weeks later, splenocytes from immunized mice were cultured in the presence of the $L^d$-restricted β-$gal_{876-884}$ peptide for 6 days and subsequently tested in a microcytotoxicity assay. Cultured splenocytes from mice immunized with the three transfectant influenza A viruses expressing the β-gal epitope (MINIGAL, NAGAL and BHAGAL viruses) were capable of specific recognition of CT26.CL25 cells or of CT26.WT cells pulsed with synthetic peptide (FIG. 3). No specific recognition was elicited by wild-type virus, or by the control transfectant viruses.

6.2.4. Treatment of Tumors Established for Three Days by Vaccination with Transfectant Influenza A Viruses Specific cytolytic responses were elicited in mice by the transfectant influenza A viruses expressing the β-$gal_{876-884}$ peptide. To evaluate whether these responses had any impact on the growth of tumor cells, we immunized mice bearing CT26.CL25 tumors established for three days with our panel of recombinant immunogens. As shown in FIG. 4, treatment of mice with MINIGAL, NAGAL or BHAGAL viruses resulted in a statistically significant reduction of the number of lung metastases. In some instances, treated mice did not show any macroscopic evidence of lung tumors by day 12.

6.3. Discussion

The results demonstrate that transfectant influenza A viruses expressing a single tumor antigen determinant can mediate the regression of an experimental murine cancer established for three days, thereby inducing a therapeutic antitumor response in mice. In clinical cancer trials at the National Cancer Institute and elsewhere, the recombinant viral vectors that are currently in use include E1-deleted adenoviruses and two recombinant poxviruses: vaccinia and fowlpox viruses. These virus vectors have been engineered to express selected human TAA. It has been shown previously that adenovirus- and poxvirus-based vectors are also able to induce tumor clearance in experimental murine cancer models (Wang, et al., 1995, J. Immunol. 154:4685-4692; McCabe, et al., 1995, Cancer Res. 55:1741-1747; Chen, et al., 1996, J. Immunol. 156:224-231). However, most cancer patients encountered in clinical settings appear to have high circulating levels of neutralizing titers to the adenovirus vectors commonly used. The same is true for vaccinia viruses, where the vast majority of patients have received the virus as children during the effort by the World-Health Organization's effort to eradicate smallpox world-wide. Indeed, many patients can also have neutralizing antibodies to many strains of the influenza A virus. However, humans are susceptible to repeated bouts of influenza-mediated upper respiratory symptoms because influenza viruses can almost endlessly change the antigenic characteristics of their viral coat.

Epidemiologists around the world attempt to predict which coat will be the most evolutionarily successful in any given year. Tumor immunotherapists must do exactly the opposite, that is, study their target cancer-bearing cohort(s) of patients, then choose a viral coat that has not penetrated that population either because of unsuccessful penetration or because the cohort of patients to receive therapeutic immunization was not yet born when penetration occurred. The latter case would involve, for example, the use of an influenza virus vector bearing a viral coat from 1934 and expressing a selected TAA to treat a population that was under age 60.

In the case of fowlpox virus vectors, there are no problems of preexisting immunity against the vector. However, poxviruses are highly complex viruses that express many different immunosuppressor proteins (Moss, 1996, in Virology, Fields, et al., eds., Philadelphia, Lippincott-Raven, pp. 2637-2671). This and the nonreplicative nature of the vector in humans might contribute to the induction of suboptimal immune responses by the vector against their expressed TAA. Furthermore, repeated administrations of the same vector to boost the cellular immune responses are usually not successful. Thus, the first administration of the vector results in the induction of neutralizing antibodies against the vector that hamper its ability to subsequently reinfect the same patient. This could be circumvented by combined immunizations with two different vectors sharing the same TAA. A very promising protocol involves the use of an influenza virus vector to prime an immune response against the expressed TAA, followed by a poxvirus vector expressing the same TAA for boosting. It has been shown that this protocol of immunization is extremely efficient in mice for the induction of powerful specific CTL responses against foreign malarial antigens which are expressed by the vectors (Murata, et al., 1996, Cell. Immunol. 173:96-107).

Another advantage of the use of influenza virus vectors to express TAA is their antigenic simplicity. Influenza A virus encodes only ten proteins, as compared to the 185 open reading frames of vaccinia virus. Thus, the proportion of the expressed desired antigen among other viral antigens is higher for influenza virus than for adenovirus or poxvirus vectors. We have engineered three influenza virus vectors expressing the same β-gal epitope in different contexts. Among these three transfectant viruses, BHAGAL virus, which express the β-gal epitope in the context of the HA gene, is expected to express higher levels of the epitope than the other two viruses, MINIGAL and NAGAL, which express the β-gal-epitope in the context of the NA gene. Thus, the HA gene expression levels are approximately 5-10 times higher than the NA gene expression levels. On the other hand, the MINIGAL virus might more efficiently deliver the epitope to MHC class I molecules due to the use of a leader sequence in front of the epitope. Finally, one might also expect differences in the efficiency of processing of the β-gal epitope according to the different flanking amino acid sequences that are present in the three viral vectors. However, all of the three viruses were able to induce a therapeutic immune response against tumors expressing β-gal in mice. Future experiments are needed to precisely compare the levels of CTL activation induced by the virus vectors against the β-gal epitope.

Safety is one major concern in the use of influenza virus vectors in humans. The use of nontransmissible, attenuated cold-adapted influenza virus vectors provides a means to safely administer the vector to humans. These cold-adapted strains have been obtained by the propagation of the virus at progressively lower temperatures, resulting in the selection and accumulation of mutations responsible for both cold-adaptation and attenuation. Alternatively, the administration of transfectant influenza viruses by routes different from the respiratory route can also provide a safe way to use these vectors in humans. Thus, influenza A viruses are able to productively infect the respiratory epithelium, but they do cause neither viral shedding nor disease when administered by non respiratory routes, such as intravenously, intraperitoneally, intramuscularly or subcutaneously, for example. However, these routes of administration are equally effective as the intranasal route in eliciting a cellular immune response against expressed antigens by the influenza virus vectors (Murata, et al., 1996, Cell. Immunol. 173:96-107). In fact, the mouse immunizations described in this communication were done intraperitoneally and they resulted in both an induction of CTLs against the model TAA and in tumor regression.

The capacity of influenza A viruses to infect dendritic cells and to express their genes at high levels is an important one. Dendritic cells are potent activators of T lymphocyte-dependent immune responses. They have a remarkably high density of both MHC class I and class II on their surfaces together with costimulatory molecules like B7-1/CD80 and B7-2/CD86, as well as other T cell activating ligands including ICAM-1/CD54. Dendritic cells infected with influenza viruses expressing TAA ex vivo, then reinfused, could be used to activate anti-tumor T cells in vivo. (In fact, the elicitation of potent anti-tumor immunity described in this example might be mediated by the infection of dendritic cells in vivo). One alternative scenario involves the use of dendritic cells infected with influenza viruses encoding TAA to generate in vitro activated anti-tumor T cells that can subsequently be adoptively transferred. A similar strategy has been used with considerable success by Greenberg and colleagues to generate anti-CMV reactivities using recombinant vaccinia-virus infected dendritic cells. However, vaccinia viruses are about 20 fold more antigenically complex and they are thus much more likely to elicit irrelevant reactivities than an influenza A virus vector.

These results support the use of influenza virus vectors in cancer therapy. In our murine cancer system, the tumorigenic properties of the cell line CT26.CL25 remain unchanged upon expression of the model TAA β-gal. This resembles the situation in most human tumors, which express TAA but are not able to induce an immune response against their TAA. Hence the results suggest that influenza viruses expressing identified human TAA will be efficacious in the treatment of human tumors. The development of influenza virus vectors expressing human TAA will advance the field of cancer therapy towards new therapeutic strategies to treat human tumors and prolong survival.

The present invention is not to be limited in scope by the specific embodiments described which are intended as single illustrations of individual aspects of the invention, and any constructs, viruses or enzymes which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various publications are cited herein, the disclosures of which are incorporated by reference in their entireties.

What is claimed is:

1. A method of inducing an immune response against a tumor-associated antigen or an epitope of a tumor-associated antigen in a patient, comprising administering to a patient in need thereof an immunogenic composition consisting essentially of an effective amount of a recombinant influenza virus and a pharmaceutically acceptable carrier, wherein the genome of the virus contains a region encoding the tumor-associated antigen or the epitope of a tumor-associated antigen.

2. The method of claim 1, wherein the region of the genome of the virus encoding the tumor-associated antigen or epitope of a tumor-associated antigen is inserted into an open reading frame of a genomic segment of the influenza virus.

3. The method of claim 2, wherein said genomic segment is a structural gene of the influenza virus.

4. The method of claim 3, wherein said structural gene is hemagglutinin (HA) or neuraminidase (NA).

5. The method of claim 1, wherein said tumor-associated antigen is a melanoma antigen.

6. The method of claim 1, wherein said tumor-associated antigen is a nonmelanoma antigen.

7. The method of claim 6, wherein said nonmelanoma antigen is a breast, ovarian, cervical or pancreatic antigen.

8. The method of claim 1, wherein said tumor-associated antigen is gp100, MART-1/MelanA, TRP-1 (gp75), tyrosinase, MAGE-1, MAGE-3, BAGE, GAGE-1, GAGE-2, N-acetylglucosaminyltransferase-V, p15, b-catenin, MUM-1, CDK4, Her-2/neu, human papillomavirus-E7 or MUC-1.

9. The method of claim 1, wherein said recombinant influenza virus is attenuated.

10. The method of claim 1, wherein a dosage of between $10^6$ and $10^7$ plaque forming units of the recombinant influenza virus is administered to the patient.

11. The method of claim 1, wherein said immunogenic composition is administered through a mucosal membrane or surface, or by a non-respiratory route.

12. The method of claim 1, wherein said immunogenic composition is administered intravenously, intraperitoneally, intramuscularly, subcutaneously, by pulmonary administration, or intranasally.

13. The method of claim 1, wherein the patient is human.

* * * * *

SEQUENCE LISTING

```
<160> NUMBER OF SEQ ID NOS: 4

<210> SEQ ID NO 1
<211> LENGTH: 9
<212> TYPE: PRT
```

-continued

```
<213> ORGANISM: Artificial Sequence
<220> FEATURE:
<223> OTHER INFORMATION: Beta-gal epitope

<400> SEQUENCE: 1

Thr Pro His Pro Ala Arg Ile Gly Leu
 1               5


<210> SEQ ID NO 2
<211> LENGTH: 27
<212> TYPE: PRT
<213> ORGANISM: Artificial Sequence
<220> FEATURE:
<223> OTHER INFORMATION: Leader peptide and beta-gal epitope

<400> SEQUENCE: 2

Met Arg Tyr Met Ile Leu Gly Leu Leu Ala Leu Ala Ala Val Cys Ser
 1               5                  10                  15

Ala Ala Thr Pro His Pro Ala Arg Ile Gly Leu
            20                  25


<210> SEQ ID NO 3
<211> LENGTH: 7
<212> TYPE: PRT
<213> ORGANISM: Artificial Sequence
<220> FEATURE:
<223> OTHER INFORMATION: gp41 HIV-derived sequence

<400> SEQUENCE: 3

Glu Leu Asp Lys Trp Ala Ser
 1               5


<210> SEQ ID NO 4
<211> LENGTH: 9
<212> TYPE: PRT
<213> ORGANISM: Artificial Sequence
<220> FEATURE:
<223> OTHER INFORMATION: peptide inserted into the NA stalk region

<400> SEQUENCE: 4

Ser Tyr Val Pro Ser Ala Glu Gln Ile
 1               5
```